United States Patent [19]
Verrelst et al.

[11] Patent Number: 6,143,942
[45] Date of Patent: Nov. 7, 2000

[54] OLIGOMERIZATION AND CATALYSTS THEREFOR

[75] Inventors: Wim Herman Verrelst, Edegem; Luc Roger Marc Martens, Meise, both of Belgium

[73] Assignee: Exxon Chemical Patents Inc., Houston, Tex.

[21] Appl. No.: 08/696,896

[22] PCT Filed: Feb. 22, 1995

[86] PCT No.: PCT/EP95/00667

§ 371 Date: Oct. 22, 1996

§ 102(e) Date: Oct. 22, 1996

[87] PCT Pub. No.: WO95/22516

PCT Pub. Date: Aug. 24, 1995

[30] Foreign Application Priority Data

Feb. 22, 1994 [GB] United Kingdom .................... 9403367
Sep. 28, 1994 [GB] United Kingdom .................... 9419664

[51] Int. Cl.[7] .................................................. C07C 2/12
[52] U.S. Cl. ............................ 585/533; 502/67; 502/71; 502/77
[58] Field of Search .............................. 585/533; 502/67, 502/71, 77

[56] References Cited

U.S. PATENT DOCUMENTS

| | | | |
|---|---|---|---|
| 3,702,886 | 11/1972 | Argauer .................................. | 423/702 |
| 4,032,432 | 6/1977 | Owen ........................................ | 208/70 |
| 4,247,416 | 1/1981 | Doherty et al. .......................... | 252/428 |
| 4,324,940 | 4/1982 | Dessau ..................................... | 585/466 |
| 4,417,086 | 11/1983 | Miller ..................................... | 585/530 |
| 4,481,177 | 11/1984 | Valyocsik ................................. | 502/77 |
| 4,556,477 | 12/1985 | Dwyer ...................................... | 208/111 |
| 4,642,404 | 2/1987 | Shihabi .................................... | 585/415 |
| 4,754,096 | 6/1988 | Chang et al. ............................ | 585/533 |
| 4,919,896 | 4/1990 | Harandi et al. .......................... | 422/142 |
| 4,973,781 | 11/1990 | Valyocsik et al. ....................... | 585/467 |
| 4,975,401 | 12/1990 | Kaeding et al. .......................... | 502/67 |
| 5,177,282 | 1/1993 | Nierlich et al. .......................... | 585/329 |
| 5,243,112 | 9/1993 | Chester et al. ............................ | 585/12 |
| 5,278,114 | 1/1994 | Wielers et al. ........................... | 502/67 |

FOREIGN PATENT DOCUMENTS

| | | |
|---|---|---|
| 169 025 | 1/1986 | European Pat. Off. . |
| 174 121 | 3/1986 | European Pat. Off. . |
| 293 914 | 12/1988 | European Pat. Off. . |
| 311310 | 4/1989 | European Pat. Off. . |
| 2106131 | 4/1983 | United Kingdom . |
| WO 93/25475 | 12/1993 | WIPO . |
| WO 93/25476 | 12/1993 | WIPO . |

OTHER PUBLICATIONS

"Estimation of the void structure and pore dimensions of molecular sieve zeolites using the hydroconversion of n–decane," Martens et al., *Zeolites*, vol. 4, pp. 98–107, Apr., 1984.

"Exploration of the void size and structure of zeolites and molecular sieves using chemical reactions,", *Pure & Appl. Chem.*, vol. 58, No. 10, pp. 1329–1338, 1986.

*Primary Examiner*—Tom Dunn
*Attorney, Agent, or Firm*—Douglas J. Collins

[57] ABSTRACT

Oligomerization degree of olefins may be controlled by employing mixed molecular sieve catalysts. Propene may be trimerized to nonene using ZSM-5 and ZSM-22, especially in an extrudate admixture.

15 Claims, No Drawings

OLIGOMERIZATION AND CATALYSTS THEREFOR

This Appln is a 371 of PCT/EP95/00667 filed Feb. 22, 1995 which is based on GB 9403367.7 filed Feb. 22, 1994 and GB 9419664.9 filed Sep. 28, 1994.

This invention relates to oligomerization reactions, and to catalysts, more especially to molecular sieve, preferably zeolite, catalysts, and their use in such reactions.

Molecular sieve catalysts of many types have been proposed for use in numerous chemical processes. Among such processes are oligomerization reactions, especially of lower olefins, e.g., alkenes, to higher olefins, e.g., higher alkenes, for example, the oligomerization of $C_2$ to $C_6$, especially $C_3$ and $C_4$, olefins, to olefins in the $C_6$ to $C_{12}$ range.

GB-A-2106131 describes oligomerizing medium molecular weight α-olefins, e.g., $C_8$ to $C_{14}$ olefins, to form heavy olefin mixtures comprising trimers, tetramers and pentamers of the starting materials, using intermediate (0.5 to 0.65 nm) pore size zeolites or other molecular sieves as catalysts. As examples of zeolites are given HZSM-5, 11, 12, 21, 23, 35, and 38, and "crystalline admixtures" or physical admixtures of such zeolites, e.g., ZSM-5 and ZSM-11. U.S. Pat. No. 4,417,086 has a similar disclosure.

U.S. Pat. No. 4,324,940 describes, inter alia, the use as an oligomerization catalyst of ZSM-5, selectively oligomerizing smaller rather than larger molecules.

U.S. Pat. No. 4,642,404 describes the activation of an extrudate of the medium pore zeolites listed in GB-A-2106131 with steam and the resulting activity of a ZSM-5 product treated in this way as a propene oligomerization catalyst. U.S. Pat. No. 4,754,096 describes the oligomerization of propene using ZSM-5 to provide lubricant oil range hydrocarbons.

U.S. Pat. No. 4,975,401 describes the advantage of using a mixture of ZSM-5 and ZSM-12 in cracking alkyl-benzenes over the use of either catalyst alone.

U.S. Pat. No. 5,177,282 describes oligomerization of an olefin by passing it over two molecular sieves in series before being contacted with a Ni-containing catalyst; in an example ethene is passed first over a 0.3 nm pore size sieve, then over a Type 13X molecular sieve.

EP-A-293914 describes crystalline admixtures and physical mixtures of various molecular sieves and their use in oligomizeration of olefins; in one example the catalytic activities of a SAPO-11/AlPO$_4$-11 composite and physical mixtures of the two sieves are compared.

U.S. Pat. No. 4,919,896 describes the use of series reactors for oligomizeration of olefins; a number of different zeolites are proposed as catalysts.

U.S. Pat. No. 4,032,432 relates primarily to cracking, but light ends withdrawn from the reactor are contacted with a catalyst comprising a mixture of larger pore, e.g., faujasite, and smaller pore, e.g., mordenite, erionite or ZSM-5, zeolites.

U.S. Pat. No. 4,247,416 describes the preparation of ZSM-25 and mentions the possibility of its being incorporated in another unspecified zeolite as matrix.

All prior published proposals for olefin oligomerization have their advantages and disadvantages, the latter including an insufficient ability to control the extent of oligomerization. For example, in the oligomerization of propene, if ZSM-5 is employed as catalyst, the oligomer product contains a relatively low proportion of dimer, and higher proportions of trimer, tetramer and pentamer. If ZSM-22 is employed as catalyst, the dimer is by far the major product. However, in neither case is the yield of trimer high. If, therefore, the desired product is one with a high nonene content neither catalyst offers an attractive route.

The present invention is based on the observation that the product obtained when oligomerization is carried out over a catalyst comprising at least two molecular sieves contains a higher proportion of a certain oligomeric species than is obtainable by carrying out the reaction over any one of the zeolite species alone.

In a first aspect, the invention provides a process for the oligomerization of an olefin, which comprises contacting under oligomerization conditions a feed comprising at least one olefin with a catalyst comprising at least one molecular sieve having a refined constraint index (as hereinafter defined) greater than 10 and at least one molecular sieve having a refined constraint index within the range of from 2 to 10 and recovering a product comprising at least one olefin oligomer.

The refined constraint index, CI°, is defined in J. A. Martens, M. Tielen, P. A. Jacobs and J. Weitkamp, Zeolites, 1984, p. 98, and P. A. Jacobs & J. A. Martens, Pure and Applied Chem., 1986, Vol. 58, p. 1329, as the ratio of 2-methylnonane to 5-methylnonane produced at 5% conversion in the hydro-isomerization of n-decane.

Examples of molecular sieves having a CI° greater than 10 include ZSM-22, ZSM-23, and certain ferrierites. Examples of molecular sieves having a CI° between 2 and 10, inclusive, include ZSM-5, 11, 12, 35, 38, 48, and 57, SAPO-11, MCM-22 and erionite, those having a CI° between 5 and 10 presently being preferred.

It is within the scope of the invention to employ mixtures containing two or more molecular sieves having a CI° of one type with one or more molecular sieves of the other type.

The molecular sieve or zeolite catalysts are advantageously ZSM-5, and ZSM-22 and ZSM-57. Zeolite ZSM-5 is described in U.S. Pat. No. 3,702,886 and in WO 93/25476, ZSM-22 is described in U.S. Pat. No. 4,556,477 and in WO 93/25475, and ZSM-57 is described in EP-A-174121 and U.S. Pat. No. 4,973,781, the disclosures of all of which are incorporated herein by reference.

In a second aspect, the invention provides a process for the oligomerization of an olefin, which comprises contacting under oligomerization conditions a feed comprising at least one olefin with a zeolite catalyst comprising ZSM-5 and ZSM-22 and recovering a product comprising at least one olefin oligomer.

A molecular sieve crystallite size advantageously up to 5 μm, preferably within the range of from 0.05 to 5 μm, more especially from 0.05 to 2 μm, and most preferably from 0.1 to 1.0 μm, may be employed.

The as-synthesized molecular sieves are advantageously converted to the acid form, generally by acid treatment, for example by HCl, or by ammonium ion exchange, and subsequent calcination. The sieves may be post-treated, as by steaming, or may be caused to contain other cations either by incorporation during preparation or by subsequent ion-exchange, examples of suitable cations being Ni, Cd, Cu, Zn, Pd, Ca, Ga, B and Ti and rare earth metals.

The two sieves are advantageously present in the catalyst in proportions by weight of 10:90 to 90:10, especially from 20:80 to 80:20, more especially from 25:75 to 75:25, for example 50:50. The optimum ratio will depend on the activity of each catalyst, with a less active component being present in a greater proportion than a more active. Accordingly, for example, since ZSM-57 appears to be more active than ZSM-5, the ZSM-57/22 ratio for an optimum trimerization of $C_3$ olefin may be lower than the ZSM-5/22 ratio. For a feed containing $C_4$ or above olefin, it is advantageous for the ZSM-22 to be present in a major proportion in a ZSM-5/ZSM-22 mixture. For a feed containing $C_3$ olefin, ZSM-5 should predominate when a $C_9$ olefin oligomer is desired.

It is within the scope of the invention for the two molecular sieves to be separate, so that the feed passes through them in series, e.g., in the form of stacked catalyst beds or reactors in series. In this case, it is advantageous for the catalyst with CI° greater than 10, e.g., ZSM-22, to be upstream of the catalyst with CI° between 2 and 10, e.g., ZSM-5 or -57 in a ZSM-5/ZSM-22 or ZSM-57/ZSM-22 combination.

Advantageously, however, the two sieves are in admixture. They may be used in the form of a homogeneous crystalline admixture, a homogeneous powder mixture, a homogeneous extrudate, or as a mixed extrudate. The extrudate advantageously contains the molecular sieves, especially the zeolites, in the desired relative proportions as indicated above, and a binder, for example alumina, silica, an aluminosilicate, or clay, advantageously in a proportion of from 10:90 to 90:10, preferably 20:80 to 80:20, by weight of total zeolite to binder. The sieves and binder may be composited by, for example, intimately mixing them together in the presence of water, and extruding or otherwise shaping, e.g., by pelletizing.

The feed olefin advantageously contains from 2 to 12 carbon atoms, and preferably from 2 to 6 carbon atoms; more preferably, the olefin feed advantageously contains propene, butenes and/or pentenes.

Reaction conditions for the oligomeration process of the invention may be, with the exception of the use of the dual catalyst, in accordance with conditions operative for prior art processes oligomerizing the same olefin.

The olefin may, for example, be fed to the catalyst in admixture with an inert diluent, e.g., a saturated hydrocarbon, in the liquid or, preferably, the gaseous, phase. For a feed comprising propene, a suitable diluent is propane, advantageously in proportions of propene:propane from 10:90 to 60:40, especially about 50:50 by weight. The feed is advantageously hydrated; preferably it contains from 0.05% to 2% by weight water. The desired proportion of water may be incorporated by saturating the feed at an appropriate temperature, e.g., from 25 to 60° C., or by injecting water through a pump.

The oligomerization may take place at a temperature advantageously in the range of from 170° C. to 300° C., preferably from 170° C. to 260° C., and most preferably from 180° C. to 260° C., at a pressure advantageously in the range of from 5 to 10 MPa, preferably from 6 to 8 MPa, and at an olefin hourly space velocity advantageously in the range 0.1 to 20, preferably from 1 to 10, and most preferably 1.5 to 7.5, whsv.

As will be apparent from the results below, the present invention makes possible a wider choice of product mix than is available by oligomerization using a single catalyst. Accordingly, the invention also provides the use in an olefin oligomerization reaction of a two molecular sieve catalyst system, especially a ZSM-5/ZSM-22 catalyst system, to control the oligomer product distribution.

The invention further provides the use of a two molecular sieve catalyst system, especially a ZSM-5/ZSM-22 system, to control, more especially to maximize, the proportion of nonenes resulting from the oligomerization of propene.

The present invention still further provides a process for the manufacture of a nonene-containing product, which comprises contacting a propene-containing feedstock under oligomerization conditions with a molecular sieve catalyst comprising ZSM-5 and ZSM-22.

The invention further provides an admixture of ZSM-5 and ZSM-22 zeolites in the form of an extrudate and an admixture of ZSM-57 and ZSM-22 zeolites, in each case advantageously in proportions of 10:90 to 90:10 by weight.

It has surprisingly been found that the catalyst mixtures have greater stability, in the sense of retaining their oligomerization catalytic activity, than the component catalysts alone. The invention accordingly also provides the use of the molecular sieve catalyst mixtures to enhance catalyst activity retention.

The following examples, in which parts and percentages are by weight unless otherwise stated, illustrate the invention:

In the Examples 1 to 15, the two zeolites used, ZSM-5 (CI° 6.8) and ZSM-22 (CI° 14.4), were both received from the manufacturer as powders in calcined and acidic form. The ZSM-5 had a $SiO_2/Al_2O_3$ ratio of about 35:1, and a crystallite size of 0.1 to 0.8 $\mu$m. Homogeneous powder materials were prepared as follows:

| Sample | % ZSM-22 | % ZSM-5 |
| --- | --- | --- |
| A | 100 | 0 |
| B | 75 | 25 |
| C | 50 | 50 |
| D | 25 | 75 |
| E | 0 | 100 |

Oligomerizations were carried out under the following conditions:

Feed: 50% by weight propene in propane

Total Feed Space Velocity: 2 wt/wt.h

Feed Hydration: at 40° C.

Pressure: 7 MPa

Each reaction was commenced at a temperature within the range of 195 to 205° C., and a conversion of 85% propene or higher was maintained by adjustment of reaction temperature. Conversion product selectivity and quality (degree of branching, see below) were analysed by off-line gas chromatography.

EXAMPLES 1 TO 3 AND COMPARATIVE EXAMPLES 1 & 2

Condition: 90% propene conversion.

| | | Product Selectivity-Alkenes of C number shown | | | |
| --- | --- | --- | --- | --- | --- |
| Example | Sample | $C_6$ | $C_9$ | $C_{12}$ | $C_{15}+$ |
| Comp 1 | A | 59 | 26 | 8 | 3 |
| 1 | B | 34 | 43 | 14 | 5 |
| 2 | C | 13 | 51 | 18 | 9 |
| 3 | D | 8 | 51 | 20 | 10 |
| Comp 2 | E | 4 | 36 | 23 | 16 |

The results clearly show that using pure ZSM-22, Comparative Example 1, or pure ZSM-5, Comparative Example 2, the maximum selectivity for nonenes is limited to 36. Using a mixed catalyst according to the invention, nonene selectivity is raised to 51.

In contrast, the selectivities for $C_6$, $C_{12}$ and $C_{15}+$ of the mixtures are substantially linear progressions between the pure zeolites. While the applicants do not wish to be bound by any theory, it appears that in the mixed catalyst examples hexenes produced by ZSM-22 are converted in situ by ZSM-5 by reaction with propene to the desired nonenes.

The degrees of branching of the nonenes produced by the catalysts were measured.

| Catalyst mixture | Propene conversion % | linear | mono | di | tri | Degree of Branching |
|---|---|---|---|---|---|---|
| A | 92.4 | 0.09 | 34.56 | 54.35 | 10.59 | 1.75 |
| B | 88.0 | 1.82 | 21.11 | 68.44 | 8.63 | 1.84 |
| C | 89.0 | 0.98 | 13.11 | 77.86 | 8.05 | 1.93 |
| D | 91.8 | 0.93 | 12.78 | 78.34 | 7.96 | 1.93 |
| E | 91.5 | 0 | 8.52 | 83.39 | 9.09 | 2.01 |

The degree of branching for Samples B to D ranges between the values for the pure catalysts, and the proportions of mono and di branched isomers produced by the mixtures also make linear progressions.

EXAMPLES 4 TO 15

In these Examples, the effect of varying propene conversion on the degree of branchiness was investigated for catalyst mixtures B, C and D.

| Example | Catalyst mixture | Propene conversion % | linear | mono | di | tri | Degree of Branching |
|---|---|---|---|---|---|---|---|
| 4 | B | 100 | 1.98 | 27.42 | 63.15 | 7.46 | 1.76 |
| 5 |   | 94.1 | 2.12 | 25.96 | 65.00 | 6.92 | 1.77 |
| 6 |   | 88.0 | 1.82 | 21.11 | 68.44 | 8.63 | 1.84 |
| 7 |   | 84.6 | 0.21 | 21.43 | 69.20 | 9.16 | 1.87 |
| 8 | C | 100 | 0.0 | 27.66 | 65.52 | 8.82 | 1.81 |
| 9 |   | 99.0 | 0.0 | 18.38 | 74.45 | 7.17 | 1.89 |
| 10 |   | 95.8 | 1.38 | 18.89 | 72.82 | 6.92 | 1.85 |
| 11 |   | 89.0 | 0.98 | 13.11 | 77.86 | 8.05 | 1.93 |
| 12 | D | 100 | 2.12 | 27.92 | 58.17 | 11.79 | 1.80 |
| 13 |   | 98.2 | 1.30 | 17.34 | 73.88 | 7.48 | 1.88 |
| 14 |   | 91.8 | 0.93 | 12.78 | 78.34 | 7.96 | 1.93 |
| 15 |   | 78.7 | 0.80 | 10.38 | 80.48 | 8.34 | 1.96 |

The results show that the degree of branching is influenced by the conversion rate, the proportion of di-branching falling, and that of mono-branching rising, as conversion rate approaches 100% in all cases.

EXAMPLE 16 AND COMPARATIVE EXAMPLES 3, 4 AND 5

In these Examples ZSM-22 and ZSM-57 (CI° 2.0) were used. Oligomerizations were carried out under the following conditions:

Feed: 12% by weight propene in propane
Temperature: 245° C.
Propene Space Velocity: See Table (WHSV)
Pressure: 6.8 MPa
The results are shown in the Table below.

| Example | Ratio ZSM-22:ZSM-57 | Propene WHSV | Propene Conv., % | Product Selectivity % $C_6$ | $C_9$ | $C_{12}$ | $C_{15}^+$ |
|---|---|---|---|---|---|---|---|
| Comp 3 | 100:0 | 4.5 | 92 | 56 | 27 | 9 | 3 |
| 16 | 50:50 | 5.6 | 94 | 18 | 34 | 17 | 12 |
| Comp 4 | 0:100 | 8 | 95 | 10 | 24 | 20 | 20 |
| Comp 5 | 0:100 | 3.7 | 94 | 8 | 27 | 21 | 24 |

Activation: Comp. 3: Calcination at 400° C. in air; Example 16 and Comps. 4 and 5: ammonium exchange followed by calcination in air at 400° C.

The mixed catalyst also has a greater stability, as shown by its ability to maintain a high propene conversion for long periods on stream.

| Example | g. propene per g. catalyst | | | | | |
|---|---|---|---|---|---|---|
|   | 30 | 45 | 60 | 100 | 125 | 150 |
| Comp 3 | 97 | 98.6 | 98.3 | 96.6 | 93.5 | — |
| 16 | 99.5 | 99.4 | 99.3 | 99.0 | 96.5 | 93.2 |
| Comp 5 | 100 | 81 | 58 | — | — | — |

COMPARATIVE EXAMPLES 6 TO 8

In these Examples, ZSM-22 and zeolite Beta (CI° 1.4) were used, alone and in admixture. Oligomerizations were carried out under the following conditions:

Feed: see Table
Temperature: 200° C.
Propene Space Velocity: see Table
Pressure: 6.8 MPa
The results are shown in the Table below:

| Example | ZSM-22:Beta | Propene WHSV | % Propene in propane | Propene Conv., % | Product Selectivity % $C_6$ | $C_9$ | $C_{12}$ | $C_{15}^+$ |
|---|---|---|---|---|---|---|---|---|
| Comp 6 | 100:0 | 20 | 50 | 94 | 49 | 28 | 12 | 7 |
| Comp 7 | 75:25 | 19 | 50 | 94 | 29 | 27 | 18 | 15 |
| Comp 8 | 0:100 | 8 | 12* | 91 | 10 | 15 | 21 | 21 |

Comp. 8, using 100% Zeolite Beta was carried out at 12% propene content because of the low time-on-stream stability of pure H-Beta. As is apparent from the results, product selectivity of the mixture was between those of the two pure zeolites. This was also true of the stability.

What is claimed is:

1. A process for the oligomerization of an olefin comprising contacting under oligomerization conditions a feed comprising at least one olefin with a catalyst comprising at least one zeolite having a refined constraint index (CI°) greater than 10 and at least one zeolite having a CI° within the range of from 2 to 10, and recovering a product comprising at least one olefin oligomer, said zeolites being present in a proportion within the range of 10:90 to 90:10 by weight.

2. The process of claim 1 wherein the catalyst comprises ZSM-22 and ZSM-5.

3. The process of claim 1 wherein the catalyst comprises ZSM-22 and ZSM-57.

4. The process of claim 1 wherein said at least one olefin contains from 2 to 12 carbon atoms.

5. The process of claim 4 wherein said at least one olefin contains from 2 to 6 carbon atoms.

6. The process of claim 5 wherein said at least one olefin is propene.

7. The process of claim 1 wherein said feed contains a butene or a pentene.

8. The process of claim 1 wherein said catalyst contains the two zeolites in a proportion within the range of from 75:25 to 25:75 by weight.

9. The process of claim 1 wherein said feed passes through the two zeolites of the catalyst in series.

10. The process of claim 9 wherein said at least one zeolite having a CI° greater than 10 comprises ZSM-22, and said ZSM-22 is upstream of ZSM-5 or ZSM-57.

11. The process of claim 1 wherein said catalyst is in the form of an extrudate.

12. The process of claim 1 wherein said at least one olefin is fed to said catalyst in admixture with an inert diluent.

13. The process of claim 1 wherein said feed is hydrated.

14. The process of claim 1 carried out at a reactant space velocity of from 1.5 to 7.5 whsv.

15. The process of claim 1 wherein said at least one olefin is propene, said catalyst comprises ZSM-5 and ZSM-22, and said at least one olefin oligomer is nonene.

* * * * *